(12) United States Patent
Gillespie et al.

(10) Patent No.: US 7,985,593 B2
(45) Date of Patent: Jul. 26, 2011

(54) APPARATUS AND METHOD FOR POLYMER CHARACTERIZATION

(75) Inventors: David T. Gillespie, Pearland, TX (US); Colin Li Pi Shan, Pearland, TX (US); Lonnie G. Hazlitt, Lake Jackson, TX (US); Alexander W. DeGroot, Lake Jackson, TX (US); Peter B. Arnoudse, Lake Jackson, TX (US); Charles Allen Williams, Richwood, TX (US)

(73) Assignee: Dow Global Technologies LLC, Midland, MI (US)

( * ) Notice: Subject to any disclaimer, the term of this patent is extended or adjusted under 35 U.S.C. 154(b) by 1035 days.

(21) Appl. No.: 11/794,417

(22) PCT Filed: Jan. 19, 2006

(86) PCT No.: PCT/US2006/001803
§ 371 (c)(1),
(2), (4) Date: Jun. 28, 2007

(87) PCT Pub. No.: WO2006/081116
PCT Pub. Date: Aug. 3, 2006

(65) Prior Publication Data
US 2008/0166817 A1    Jul. 10, 2008

Related U.S. Application Data

(60) Provisional application No. 60/646,331, filed on Jan. 24, 2005.

(51) Int. Cl.
*G01N 30/02* (2006.01)
*G01N 30/30* (2006.01)

(52) U.S. Cl. ........ 436/161; 422/70; 73/61.52; 73/61.56; 210/198.2; 210/656

(58) Field of Classification Search .................. 436/161; 422/70; 73/61.52, 61.56; 210/198.2, 656
See application file for complete search history.

(56) References Cited

U.S. PATENT DOCUMENTS
2006/0266708 A1 * 11/2006 Yu et al. ......................... 210/656

OTHER PUBLICATIONS

Nakano, et al, Journal of Applied Polymer Science, vol. 26, No. 12, pp. 4217-4231 (1981).
Zacur, et al, Polymer Engineering and Science, vol. 39, No. 5, pp. 921-929 (1999).
Wild, et al, Journal of Polymer Science, vol. 20, pp. 441-455 (1982).
Yau, et al., 2000 Tappi Polymers, Laminations, & Coatings Conference, pp. 699-707 (2000).
Yau, et al., Polymer 42, pp. 8947-8958 (2001).
Wild, et al., Polymer Preparation, vol. 18, p. 182 (1977).

* cited by examiner

*Primary Examiner* — Jan M Ludlow

(57) ABSTRACT

Apparatus for GPC/TREF and TREF/GPC characterization of a polymer sample. The apparatus provides for the automated and integrated use of multiple TREF columns and a GPC system employing a multiple flow through detectors. In addition, a method for TREF/GPC characterization of a polymer sample by GPC analysis of TREF fractions at increasing TREF elution temperatures from multiple TREF columns operated in a coordinated and synchronized temperature cycle for increased sample throughput. Also, a method for GPC/TREF characterization of a polymer sample by GPC fractionation followed by TREF fractionation of the GPC fractionations.

4 Claims, 3 Drawing Sheets

APPARATUS AND METHOD FOR POLYMER CHARACTERIZATION

CROSS-REFERENCE STATEMENT

This application is a 35 U.S.C. §371 National Phase Application of International Application No. PCT/US2006/001803, filed Jan. 19, 2006, which claims the benefit of U.S. Provisional Application No. 60/646,331, filed Jan. 24, 2005.

BACKGROUND

Temperature Rising Elution Fractionation (TREF) is an important separation method for characterizing the crystallinity distribution of polymers (see Wild et al., *Polym. Prepr.* 18, 182 (1977) and Wild et al., *J. Polym. Sci.*, 20, 441 (1982)). The crystallinity distribution is primarily a function of short chain branching content and controls solid state properties such as density. In general, a nearly linear correlation between elution temperature and short chain branching frequency is observed in an TREF analysis of a semi-crystalline polymer such as "polyethylene" and "polypropylene".

Gel Permeation Chromatography (GPC) is an important separation method for characterizing the size distribution of polymers. The size distribution of is primarily a function of molecular weight and controls melt properties such as rheology. In general, a logarithmic correlation between molecular weight and elution volume is observed in GPC analysis of a polymer.

Nakano and Goto, *J. Appl. Polym. Sci.*, 24, 4217 (1981) described a TREF/GPC system that provided valuable cross-fractionation characterization of polymer samples. However, the system of Nakano and Goto is not capable of more than one analysis per working day. Therefore, it would be an advance in the art of polymer characterization if a TREF/GPC or GPC/TREF system could be developed that was capable of an increased number of analyses per working day. There is no mention in the prior art of a GPC/TREF system. However, it would be an advance in the art if a system for GPC/TREF were invented.

SUMMARY OF THE INVENTION

The instant invention is a solution, at least in part, to the above-mentioned problems. The instant invention is an apparatus capable of increased TREF/GPC characterizations per work day. The apparatus of the instant invention can also be used for GPC/TREF characterization of polymer samples.

More specifically, the instant invention is a method for TREF/GPC characterization of one or more polymer samples, comprising the steps of: (a) introducing a sample of a first polymer to be characterized into a stream of solvent flowing through a first TREF column; (b) stopping the flow of the solvent when the sample is in the first TREF column; (c) cooling the first TREF column to precipitate at least a portion of the sample in the TREF column; (d) heating the first TREF column to a first temperature to dissolve a portion of the sample precipitated in step (c) to form a first solution of dissolved first sample; and (e) analyzing the first solution of dissolved first sample by gel permeation chromatography.

In another embodiment, the instant invention is a method for GPC/TREF characterization of a polymer sample, comprising the steps of: (a) introducing a sample of a polymer to be characterized into a stream of eluent flowing through a gel permeation chromatography column to produce successive elution volumes from the gel permeation chromatography column wherein the polymer sample elutes therefrom substantially according to the molecular size distribution of the polymer sample; (b) flowing a first elution volume from the gel permeation chromatography column into a first TREF column at an elevated temperature; (c) flowing a second elution volume from the gel permeation chromatography column into a second TREF column at an elevated temperature; (d) cooling the first TREF column to precipitate polymer in the first elution volume in the first TREF column; (e) cooling the second TREF column to precipitate polymer in the second elution volume in the second TREF column; (f) flowing a stream solvent through the second TREF column while heating the second TREF column to dissolve the polymer precipitated therein into the flowing stream of solvent; (g) flowing the stream of solvent from the second TREF column of step (f) through a flow through detector to detect the polymer in the stream of solvent as the polymer dissolves in the solvent as the second TREF column is heated; (h) flowing a stream solvent through the first TREF column while heating the first TREF column to dissolve the polymer precipitated therein into the flowing stream of solvent; (i) flowing the stream of solvent from the first TREF column of step (h) through a flow through detector to detect the polymer in the stream of solvent as the polymer dissolves in the solvent as the first TREF column is heated.

In yet another embodiment, the instant invention is an apparatus capable of being used for GPC/TREF characterization of a polymer sample or for TREF/GPC characterization of a polymer sample, the apparatus comprising: (a) an eluent reservoir; (b) a pump in liquid communication with the eluent reservoir; (c) a sample injection valve in liquid communication with the pump; (d) a two position six-port valve in liquid communication with the sample injection valve; (e) a gel permeation chromatography column having an inlet and an outlet, the inlet being in liquid communication with the six-port valve, the outlet being in liquid communication with the six-port valve; (f) a flow-through infrared detector in fluid communication with the six-port valve; (g) a flow-through light scattering detector in liquid communication with the infra-red detector; (h) a flow-through viscosity detector in liquid communication with the light scattering detector; (i) a waste reservoir in liquid communication with the viscosity detector; (j) a first tee in liquid communication with the six-port valve; (k) a first on-off valve in liquid communication with the first tee; (l) a second tee in liquid communication with the six-port valve and with the first on-off valve; (m) a first oven containing elements (a)-(l); (n) a two position three port valve in liquid communication with the first tee; (o) a cross in liquid communication with the three-port valve; (p) a first temperature equilibrium conduit in liquid communication at one end thereof with the three port valve; (q) a second temperature equilibrium conduit in liquid communication at one end thereof with the cross and at the other end thereof with the other end of the first temperature equilibrium conduit; (r) a third tee in liquid communication with the first cross; (s) a fourth tee in liquid communication with the third tee; (t) a second on-off valve in liquid communication with the fourth tee; (u) a second oven containing elements (n), (o), and (q)-(t); (v) a third on-off valve in liquid communication with the first cross; (w) a fourth on-off valve in liquid communication with the second tee; (x) a fifth on off valve in liquid communication with the fourth tee; (y) a first TREF column having an inlet and an outlet, the inlet of the first TREF column being in liquid communication with the third on-off valve; (z) a second TREF column having an inlet and an outlet, the inlet of the second TREF column being in liquid communication with the fourth on-off valve; (a') a third TREF column having an inlet and an outlet, the inlet of the third TREF column being in liquid communication with the fifth on-off valve; (b') a fifth tee in liquid communication with the outlet of the first TREF column and with the second tee; (c') a sixth tee in liquid communication with the outlet of the second TREF column and with the fifth tee; (d') a seventh tee in liquid communication with the outlet of the third TREF column and the second on-off valve; (e') a third oven containing elements (v) and (w); (f') a fourth oven for containing elements (x) and (y); (g') a fifth oven for containing elements (z) and (a'); (h') a sixth oven for containing elements (b'), (c') and (d').

DETAILED DESCRIPTION OF THE INVENTION

Figure 1:
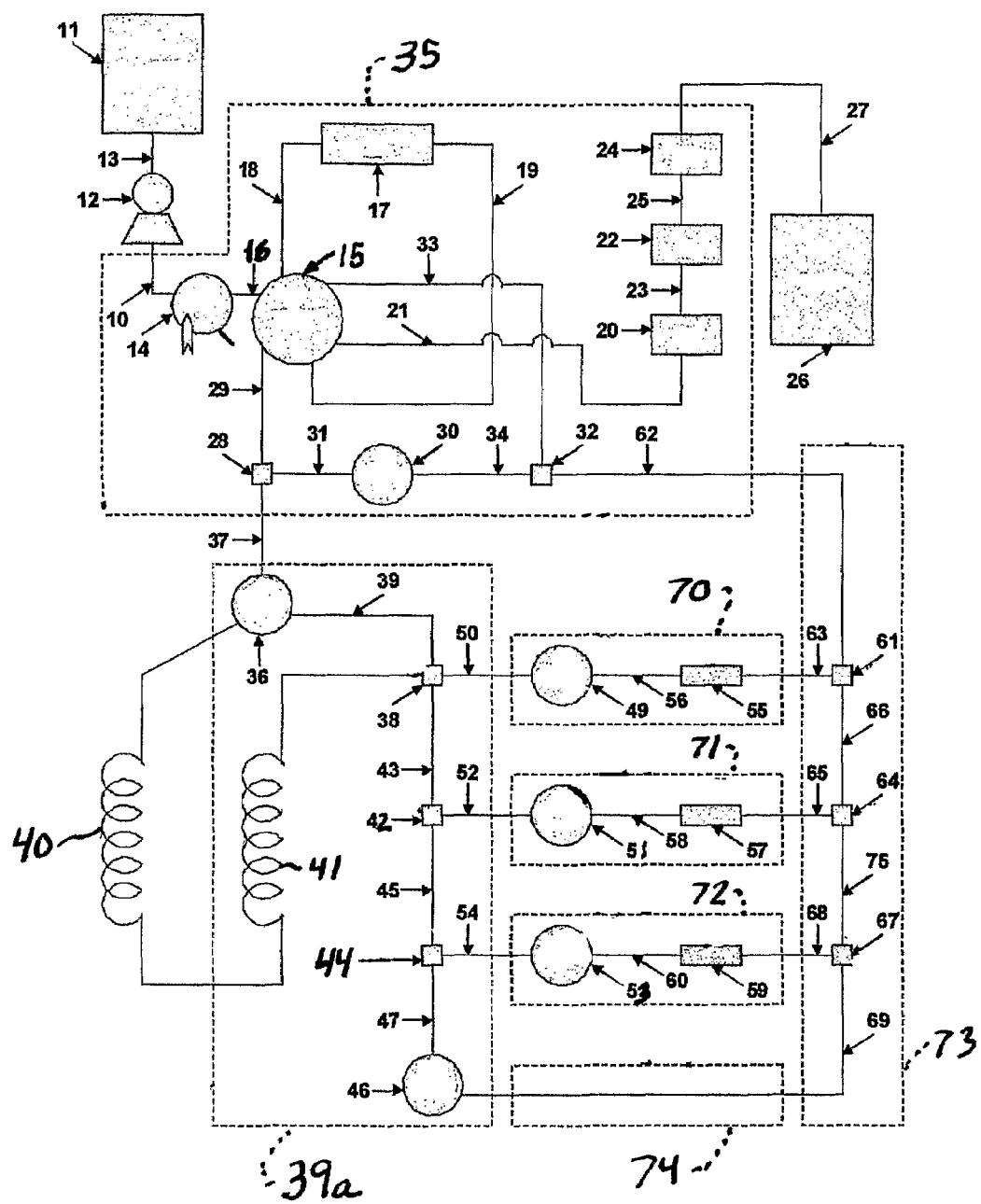
FIG. 1 is a schematic drawing of a preferred apparatus embodiment of the instant invention.

Referring now to FIG. 1, therein is shown a schematic drawing of a preferred apparatus of the instant invention including an eluent reservoir 11. A pump 12 is in liquid communication with the eluent reservoir 11 by way of tubing 13. A sample injection valve 14 is in liquid communication with the pump 12 by way of tubing 10. A two position six-port valve 15 is in liquid communication with the sample injection valve 14 by way of tubing 16. Gel permeation chromatography column 17 has an inlet and an outlet, the inlet being in liquid communication with the six-port valve 15 by way of tubing 18, the outlet being in liquid communication with the six-port valve 15 by way of tubing 19. A flow-through infrared detector 20 is in fluid communication with the six-port valve 15 by way of tubing 21. A flow-through light scattering detector 22 is in liquid communication with the infra-red detector 20 by way of tubing 23. A flow-through viscosity detector 24 is in liquid communication with the light scattering detector 22 by way of tubing 25. A waste reservoir 26 is in liquid communication with the viscosity detector 24 by way of tubing 27. A first tee 28 is in liquid communication with the six-port valve 15 by way of tubing 29. A first on-off valve 30 is in liquid communication with the first tee 28 by way of tubing 31. A second tee 32 is in liquid communication with the six-port valve 15 by way of tubing 33 and with the first on-off valve 30 by way of tubing 34. A first temperature controlled oven 35 contains elements 14-34.

Referring still to FIG. 1, a two position three port valve 36 is in liquid communication with the first tee 28 by way of tubing 37. A cross 38 is in liquid communication with the three-port valve 36 by way of tubing 39. A first temperature equilibrium conduit 40, shown as a coiled tube, is in liquid communication at one end thereof with the three port valve 36. A second temperature equilibrium conduit 41, shown as a coiled tube, is in liquid communication at one end thereof with the cross 38 and at the other end thereof with the other end of the first temperature equilibrium conduit 40. A third tee 42 is in liquid communication with the first cross 38 by way of tube 43. A fourth tee 44 is in liquid communication with the third tee 42 by way of tubing 45. A second on-off valve 46 is in liquid communication with the fourth tee 44 by way of tubing 47. A second temperature controlled oven 39a contains elements 36, 38, 39, and 41-47. A third on-off valve 49 is in liquid communication with the first cross 38 by way of tubing 50. A fourth on-off valve 51 is in liquid communication with the second tee 42 by way of tubing 52. A fifth on off valve 53 is in liquid communication with the fourth tee 44 by way of tubing 54.

Referring still again to FIG. 1, a first TREF column 55 having an inlet and an outlet is provided wherein the inlet of the first TREF column 55 is in liquid communication with the third on-off valve 49 by way of tubing 56. A second TREF column 57 having an inlet and an outlet is provided wherein the inlet of the second TREF column 57 is in liquid communication with the fourth on-off valve 51 by way of tubing 58. A third TREF column 59 is provided having an inlet and an outlet, the inlet of the third TREF column 59 being in liquid communication with the fifth on-off valve 53 by way of tubing 60. A fifth tee 61 is in liquid communication with the outlet of the first TREF column 55 by way of tubing 63 and with the second tee 32 by way of tubing 62. A sixth tee 64 is in liquid communication with the outlet of the second TREF column 57 by way of tubing 65 and with the fifth tee 61 by way of tubing 66. A seventh tee 67 is in liquid communication with the outlet of the third TREF column 59 by way of tubing 68 and with the sixth tee 64 by way of tubing 75 and also with the second on-off valve 46 by way of tubing 69. A third temperature controlled oven 70 contains the first TREF column 55. A fourth temperature controlled oven 71 contains the second TREF column 57. A fifth temperature controlled oven 72 contains the third TREF column 59. A sixth temperature controlled oven 73 contains the tees 61, 64 and 67. A seventh temperature controlled oven 74 contains a portion of the conduit 69.

While the apparatus in FIG. 1 has been described as having preferred aspects, the instant invention can be further modified within the spirit and scope of this disclosure. This application is therefore intended to cover any variations, uses, or adaptations of the present invention using the general principles disclosed herein. For example, although the use of all three detectors 20, 22 and 24 is preferred, such use is not critical in the instant invention. Similarly, although three TREF columns 55, 57 and 59 are described above, only two such columns are critical in the instant invention and more than three can also be used. And, as a further example, any suitable multi-port valve can be plumbed according to the broad scope of the instant invention in place of valve 14 of FIG. 1.

The instant invention is also method for GPC/TREF characterization of a polymer sample, comprising the steps of: (a) introducing a sample of a polymer to be characterized into a stream of eluent flowing through a gel permeation chromatography column to produce successive elution volumes from the gel permeation chromatography column wherein the polymer sample elutes therefrom substantially according to the molecular weight distribution of the polymer sample; (b) flowing a first elution volume from the gel permeation chromatography column into a first TREF column at an elevated temperature; (c) flowing a second elution volume from the gel permeation chromatography column into a second TREF column at an elevated temperature; (d) cooling the first TREF column to precipitate polymer in the first elution volume in the first TREF column; (e) cooling the second TREF column to precipitate polymer in the second elution volume in the second TREF column; (f) flowing a stream solvent through the second TREF column while heating the second TREF column to dissolve the polymer precipitated therein into the flowing stream of solvent; (g) flowing the stream of solvent from the second TREF column of step (f) through a flow through detector to detect the polymer in the stream of solvent as the polymer dissolves in the solvent as the second TREF column is heated; (h) flowing a stream solvent through the first TREF column while heating the first TREF column to dissolve the polymer precipitated therein into the flowing stream of solvent; (i) flowing the stream of solvent from the first TREF column of step (h) through a flow through detector to detect the polymer in the stream of solvent as the polymer dissolves in the solvent as the first TREF column is heated. It should be understood that the order of TREF column use described above can be reversed if desired. The flow through detector can be selected from the group consisting of an infrared detector, a light scattering detector and a viscosity detector. A flow through detector which is a composition detector (such as an FTIR detector) is highly preferred in the instant invention. The flow through detector is preferably followed by two additional flow through detectors selected from the group consisting of an infrared detector, a light scattering detector and a viscosity detector. One or more additional TREF columns can be used in the same manner that the first and second TREF columns are employed in the instant invention.

The instant invention is also a method for TREF/GPC characterization of one or more polymer samples, comprising the steps of: (a) introducing a sample of a first polymer to be characterized into a stream of solvent flowing through a first TREF column; (b) stopping the flow of the solvent when the sample is in the first TREF column; (c) cooling the first TREF column to precipitate at least a portion of the sample in the TREF column; (d) heating the first TREF column to a first temperature to dissolve a portion of the sample precipitated in step (c) to form a first solution of dissolved first sample; and (e) analyzing the first solution of dissolved first sample by gel permeation chromatography. Preferably, the instant invention comprises the additional steps of: (f) introducing a sample of a second polymer to be characterized into a stream of solvent flowing through a second TREF column; (g) stopping the flow of the solvent when the sample is in the second TREF column; (h) cooling the second TREF column to precipitate at least a portion of the sample in the second TREF column; (i) heating the second TREF column to a first temperature to dissolve a portion of the sample precipitated in step (h) to form a first solution of dissolved second sample; and (j) analyzing the first solution of dissolved second sample by gel permeation chromatography. Furthermore, the instant invention even further preferably further comprises the steps of: (k) heating the first TREF column to a second temperature higher than the first temperature to dissolve an additional portion of the sample precipitated in step (c) to form a second solution of dissolved first sample; (l) analyzing the second solution of dissolved first sample by gel permeation chromatography; (m) heating the second TREF column to a second temperature higher than the first temperature to dissolve an additional portion of the sample precipitated in step (h) to form a second solution of dissolved second sample; and (n) analyzing the second solution of dissolved second sample by gel permeation chromatography. Steps (e), (l), (j) and (n) are preferably carried out sequentially. As with the GPC/TREF embodiment, in the TREF/GPC the order of TREF column use described above can be reversed if desired. In addition it should be understood that the term "GPC" also encompasses the following chemical analysis procedures in the instant invention: (a) field flow fractionation; (b) solvent/non-solvent molecular weight fractionation; (c) molecular topological fractionation as described, for example, in United States Patent Publication 2005/0176154; and (d) the technique taught in U.S. Pat. No. 6,345,528 and U.S. Pat. No. 6,260,407.

Example 1

An apparatus similar to that shown in FIG. 1 is constructed and can be summarized as the combination of a Waters 150C chromatograph with an TREF oven using a heated transfer line for eluent flow between the two modules.

Several criteria are involved with the TREF oven design:
1) A forced flow gas (nitrogen) design is adopted to maximize heat transfer to the TREF flow-path.
2) The targeted heat capacity of the oven is made sufficiently high to maintain high temperature stability including heat exchange.
3) A temperature ramp rate of 100° C. per hour to heat and cool the oven is targeted to fully support an eventual multiple oven design.
4) Adequate exhausting of a large flow of an inert media such as nitrogen.
5) The oven design allows holes in the top and bottom to be drilled (electrical connections and heaters on the sidewalls) to allow for transfer into and out of the oven with an external heated transfer line.
6) The ovens are to be highly insulated to protect the surroundings from radiant heat.

The TREF columns are constructed of 316 SS 3.2 mm (0.125 inch) OD by 2 mm (0.08 inch) ID precision bore tubing. The tubing is cut and filled with a 60/40 (v/v) mix of stainless steel cut wire shot and spherical technical quality glass. The interstitial volume was approximately 1.00 ml. A surface mounted platinum resistive temperature device (rtd) is attached to the column.

When combining the TREF process with the GPC process, it is beneficial that the eluent be kept above the crystallization temperature in the solvent chosen for each polymer fraction during the loading and elution process. The TREF heated transfer line is constructed of 9.5 mm (⅜ inch) diameter stainless steel tubing. This line serviced both the eluent in and eluent out (in this case 1,2,4 trichlorobenzene (TCB)) from the GPC to the TREF unit. The interior eluent lines are 0.25 mm (0.01 inch) id×1.6 mm (1/16 inch) od tubing. The heated transfer line is wrapped with heat tape and insulated with a thick layer of glass wrap. The heated transfer line is mounted directly at the wall of the 150C at the column compartment with the inner 9.5 mm (⅜ inch) SS tubing penetrating through the "fire brick" into the column compartment. The other end of the heated transfer line is mated with the top of the TREF oven (with the 9.5 mm line and the associated 1.6 mm tubing penetrating through the insulated lid). The 1.6 mm tubing is then attached on the inside of the TREF oven and the inside of the GPC oven. The heated transfer line is successful in keeping the polymer from precipitating.

The eluent should ideally be at the same temperature as the TREF column during elution, so a means of equilibrating the solvent to the TREF column temperature is beneficial. The TREF oven is fitted with a temperature pre-equilibration coil so that the incoming elution stream would be at about the same temperature as the TREF column (during the TREF elution cycle). The pre-equilibration coil is constructed from a 50-foot length of 1 mm (0.04-inch) id tubing. The coil is placed in the bottom of the TREF oven with an approximate 15 cm (6 inch) diameter wrapped continuous coil to maximize heat transfer and minimize wall-contact surface area.

Since TCB has a very high heat capacity, at a standard flowrate of 1.0 ml/min, the TREF column (which has an interstitial volume of around 1-ml) would be significantly heated or quenched without the pre-equilibration coil. It should be noted that the pre-equilibration coil has a large volume (>12 milliliters) and therefore, is preferably only inline during the TREF elution cycle (and not the TREF loading cycle). The pre-equilibration coil with a volume of 12 ml in a 1 mm (0.04 inch) id geometry proved to be successful at equilibrating the solvent, as the TREF peak eluted at correct temperatures and of comparable width and resolution to a reference TREF system.

A thermostatically controlled nitrogen chiller is used with a nitrogen supply and is capable of discharging of 5-8° C. nitrogen, which is piped to each TREF oven for temperature control purposes.

A 2 channel IR detector is used as the primary concentration detector. The IR detector uses a pair of fixed wavelength filters tuned to the methylene stretching region (approx. 2900 cm$^{-1}$) and a non-absorbing region. The ratio of these two signals allows for temperature compensation within the IR measurement. Internal digital processing converts transmission to absorbance. At GPC concentrations, this detector proves to be highly linear in its response. Alternatively, the IR detector can be a flow through FTIR detector. While a flow through FTIR detector is more expensive than a filter IR detector, the FTIR detector provides the additional capability of composition measurement (for example, comonomer content or even other groups such as silyl or carbonyl measurement).

Signals from the thermocouples, pressure transducers, and IR detector are acquired by a high resolution data acquisition card connected to a general purpose digital computer programmed to control the system. Data collection was made at 1.5 seconds/scan for the 3 RTD temperature probes (main oven, GPC oven and transfer line) along with the IR detector and pressure transducer.

Two-position, three-port switching valves are used to divert the pump flow in the desired direction. The valve controllers are activated using a digital communication protocol. The digital switching is controlled by an Input/Output card. The valve configuration and switching is controlled by programming a digital output sequence.

Two temperature controllers equipped with serial communications and output relay modules are used to control the main TREF oven and heated transfer line. A third temperature controller is also used as an alarm for emergency high-temperature shutdown of the instrument. The temperature controllers are serially connected to the PC.

Temperature ramp profiles are initially programmed and started manually. However, the computer program can also be used to allow customizable on-line control of the temperature controllers using a flexible menu driven interface.

The computer program is written to provide an interface to control the operation of the instrument. The program handles the timing and flow sequence as a series of user-inputted command steps. Once entered, the command steps are processed sequentially. The timing for each step is calculated a priori in order to match the injection sequence from the Waters 150C. No software communication link exists between the Waters 150C and the crossfractionation software. The only timing utilized is the injection trigger for each sample injection. At the time of injection, a 5V signal is relayed through the GPC and is monitored by the software via a digital input/output card. At the trigger point a sample is injected from within the GPC injector module and would either be loaded into the TREF column or into the GPC columns.

These modules will perform discrete actions such as loading the TREF column or running a GPC from the GPC injector compartment. For example, once a sample has been loaded onto the TREF columns, the oven temperature can be changed to heat or cool at a programmed rate. After completing the temperature profile, a cooled sample can either be eluted as a continuous TREF distribution or successive, predetermined "preparative" TREF fractions can be loaded onto the GPC column by selecting the appropriate programming step. The software monitors all channels of data from the IR detector, the system pressure transducer, and temperatures of the oven and heated transfer line. The data are saved into ASCII format when data processing is required (that is GPC, TREF, or preparative TREF data).

Polyethylene samples are prepared between 2-4 mg/mL TCB depending upon the molecular weight distribution, density, and the desired number of fractions to be collected. The samples are solubilized using standard polyolefin procedures for conventional GPC depending upon the sample type, density, and melt index. A procedure that filters samples that contain colorants and additives can also be employed. The polyethylene samples are dissolved at 160° C. with gentle agitation for 2 hours and then placed in the GPC carousel at 140° C.

System flow rate is controlled at 1 milliliter per minute for both the GPC elution and the TREF elution. The GPC separation is accomplished through a series of linear mixed bed GPC columns (typically 3-4) supplied by Polymer Laboratories (UK). The GPC column compartment is operated at 145 C. to prevent precipitation when eluting from the TREF column. Sample injection is established at 500 uL. The temperature ramp rates are chosen based on the desired number of fractions and are limited by the time required for the GPC elution. Based on a 45 minute GPC run, the following temperature range and ramp rates are chosen.

Temperature Range: 30° C.-110° C.
Crystallization Rate: 0.124° C./min (10.75 hrs)
Elution Rate: 0.124° C./min (10.75 hrs)
Number of "preparative" TREF fractions: 14 (45 min×14=10.5 hrs)

Raw master data files from the cross-fractionation collection are read directly into Visual Basic for Applications™ residing in a Microsoft Excel™ framework. The program automatically sorts the master file into separate GPC files (each one representing a distinct elution temperature). The individual GPC data files are integrated using separate baseline and integration limit selections. A polystyrene calibration curve is used for referencing the molecular weight distribution data. The polystyrene standard peak molecular weights were converted to polyethylene molecular weights using the following equation (as described in Williams and Ward, J. Polym. Sci., Polym. Let., 6, 621 (1968)):

$$M\text{polyethylene} = A \times (M\text{polystyrene})^B$$

Where M is the molecular weight, A has a value of 0.4315 and B is equal to 1.0.

During a typical analysis, 14 individual TREF fractions are measured by GPC. Each TREF fraction represents approximately a 7° C.-temperature slice. The MWD of each slice is calculated from the integrated GPC chromatograms. A plot of the GPC MWD's as a function of temperature (resulting in a 3D surface plot) depicts the overall molecular weight and crystallinity distribution. In order to create a smoother 3D surface, the 14 fractions are interpolated to expand the surface plot by increasing the number of individual GPC chromatograms as part of the calculation process.

The area of the individual GPC chromatograms correspond to the amount eluted from the TREF fraction (across the 7° C.-temperature slice). The individual heights of GPC chromatograms (Z-axis on a 3D plot) correspond to the polymer weight fraction thus giving a representation of the proportion of polymer present at that level of molecular weight and crystallinity. These 3D plots can be rotated on each axis to provide a unique vantage point of the molecular structural distribution.

Figure 2:
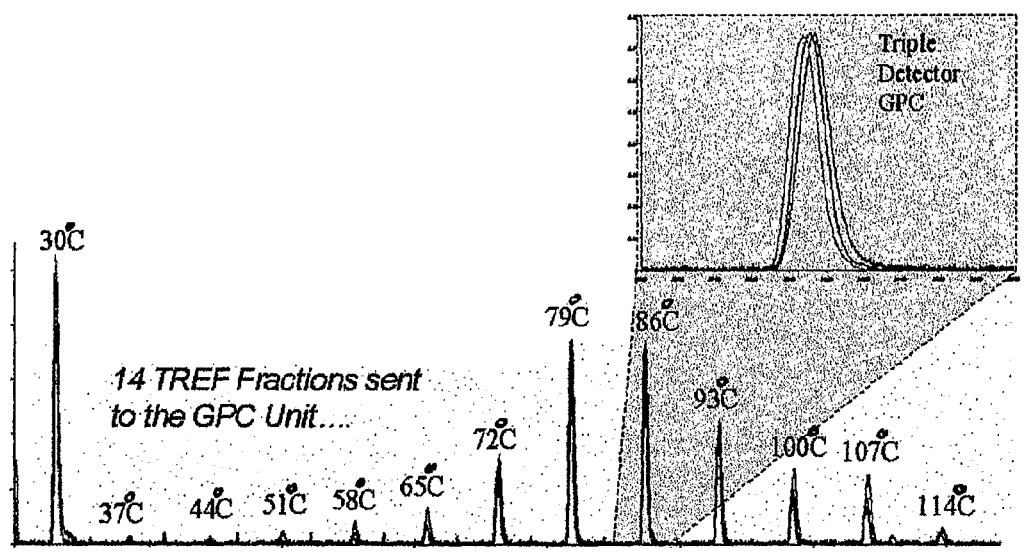
FIG. 2 depicts the TREF/GPC method embodiment of the instant invention.
Figure 3:
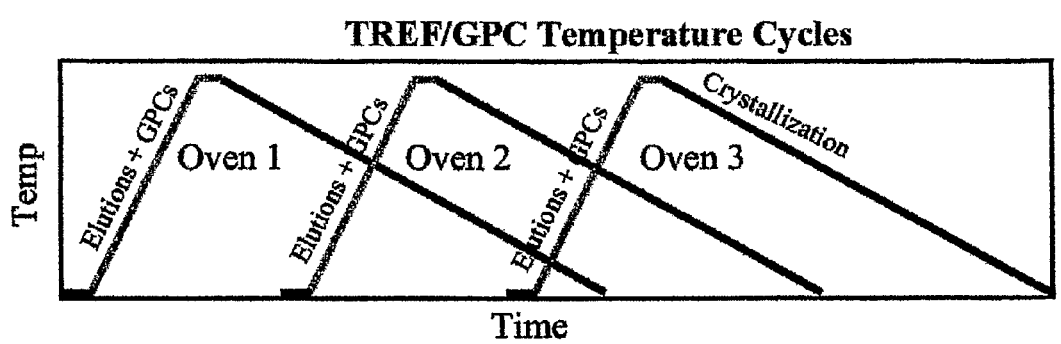
FIG. 3 depicts the synchronized oven temperature cycle for the TREF/GPC method embodiment of the instant invention.

FIG. 2 shows the data collected during a typical TREF/GPC experiment. Shown at the bottom are the 14 sequential GPC chromatograms collected over the elution temperature range in 7° C. increments. It can be seen that the height of the GPC chromatograms represent the amount of polymer elution at a given temperature slice. However, in a more complex distribution, one would use the peak areas to determine the relative weights of the TREF slices. It is clear for this polypropylene copolymer that there is a substantial amount of soluble polymer present at 30° C. and a broad short chain branching distribution centered between 58° C. and 114° C. The use of multiple TREF columns/ovens in the above described system as shown in FIG. 1 synchronized as shown in FIG. 3 significantly increases the number of polymer samples that can be characterized per day.

Example 2

The apparatus shown in FIG. 1 is assembled. The computer program is written to provide an interface to control the operation of the instrument. The program allows for custom sequencing for temperature control of the ovens, valve positions and handles the timing and flow sequence as a series of user-inputted command steps. Sample loading and injection is controlled by the Waters 150C programming interface. The timing for each step is calculated beforehand in order to match the injection sequence from the Waters 150C. No communication link exists between the Waters 150C and the crossfractionation software. The only timing available is the injection trigger for each sample injection. At the time of injection, a 5V signal is relayed through the GPC and is monitored by the software via a digital input/output card. At the point of trigger, a sample is injected from the GPC injector into the GPC columns.

Figure 4:
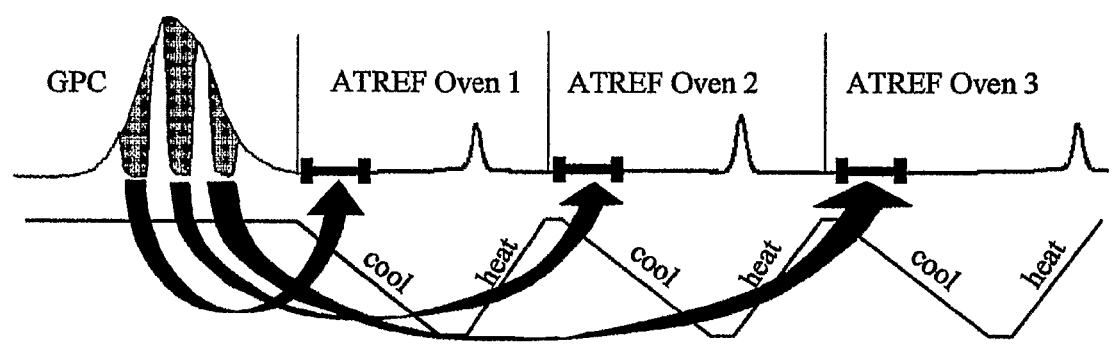
FIG. 4 depicts the GPC/TREF method embodiment of the instant invention.

In GPC-TREF operation, the eluent from the GPC can be diverted to any of the three TREF ovens as depicted in FIG. 4. In this system, the TREF column volumes are 1.5 mL which allows 1 mL GPC fractions to be collected in each column (this corresponds to 1 min of GPC retention time at a flow rate of 1 mL/min). The larger column volume ensures that the entire sample is captured in the middle of the TREF column. An additional wash step is also performed after the GPC elution has completed by purging the lines with an extra 0.1 mL of fresh solvent into the opening of each TREF column. This additional volume prevents any residual material from crystallizing in the lines during cooling.

A typical analysis consists of GPC fractionation (using a 3 column system) of a high molecular weight fraction (24-25 minutes into oven 3 equivalent to a range of 200,000-460,000 grams per mole), medium molecular weight (26-27 min into oven 2 equivalent to a range of 55,000-115,000 grams per mole) and low molecular weight (28-29 min into oven 1 equivalent to a range of 15,000-30,000 grams per molw) fraction (however, each fractionation can be customized). After the three GPC fractions have been loaded into their respective columns, the polymer is crystallized slowly at a rate of 0.3° C./min as the ovens are cooled. Once the crystallization cycle is complete, the individual TREF analyses are performed sequentially. From our experience, the LMW fraction sometimes resulted in the highest crystalline material which needed to be eluted closer to the hot GPC main oven to prevent plugging.

The TREF analysis is performed by heating the TREF oven at 1° C./min and eluting the polymer with fresh solvent. Once the elution temperature of the polymer is reached, the polymer dissolves and then flows out to the IR detector. To prevent any premature elution of the crystallized polymer, the incoming solvent temperature is preferably matched to the temperature of the TREF column during elution. The fresh solvent is directed through the temperature equilibration loop and then through the desired oven. Note, the equilibration loop itself is contained in a fourth oven and its temperature follows the profile of the TREF ovens during elution.

The TREF ovens remain at 130° C. during loading and until the crystallization cycle begins. In order to save time on the cooling cycle, the ovens are rapidly cooled from 130 to 110° C. at 2° C./min and then cooled more slowly at 0.3° C./min until 70° C. Once cooled, the TREF elution begins sequentially from oven 1 to oven 3 (LMW to HMW) from 70 to 110° C./min. One additional feature is that the equilibration oven is programmed to match the elution temperature of the TREF oven to minimize any solvent temperature differences.

The GPC conditions used are: Concentration: 2 mg/mL; Injection volume: 500 µL; Flow rate: 1 mL/min; Columns: at least one Mixed-B column (Polymer Laboratories).

It is observed that the HMW fraction eluted at the highest temperature followed by the MMW fraction (−4.7° C. from HMW) and then the LMW fraction (−5.9° C. from HMW) at the lowest temperature. For these narrow MW cuts, the elution temperature decreases with decreasing molecular weight of the cut. For interpretation of the TREF results according to the differences in crystallizability (due to branching) of each MW fraction, the elution temperature of each fraction is calibrated in reference to the MW fractions of the linear polyethylene homopolymer. A calibration offset is applied to each elution temperature to account for the observed depression of the elution temperature with decreasing molecular weight. After the calibration, the elution temperatures of linear homopolymer fractions are adjusted to be 101° C. This calibration method is then applied to a sample to make a direct comparison of the elution temperatures with the linear homopolymer for direct branching measurements. After the calibration with known standards with a known level of comonomer (as measured by $^{13}C$ NMR), a branching frequency (branches/1000C's) can be estimated from the TREF elution temperatures.

A more rigorous calibration method can also be employed by analyzing polyethylene copolymers synthesized with a homogeneous catalyst in the range of 0-3 wt % comonomer with the above method. A broad calibration curve can be developed to correlate the known comonomer contents or branching frequency (as measured by 13C NMR) with the observed elution temperatures over a broad range of molecular weights. Such a calibration curve can be applied to estimate the comonomer content or branching frequency of the molecular weight cuts from the observed TREF elution temperatures.

From the TREF profiles of the various molecular weight fractions, it is seen that the comonomer is distributed differently for each blend. Examining the HMW fractions, the conventional blend has the highest average elution temperature (98.9° C.) followed by the flat blend (98.0° C.) and then the reverse blend with the lowest elution average temperature (97.1° C.). Examining the MMW fractions, the differences in average elution temperatures between the blends are less pronounced (HMW (98.0° C.), MMW (97.9° C.), and LMW (97.6° C.). Examining the LMW fractions, the conventional blend now has the lowest elution average temperature (97.1° C.), followed by the flat blend (97.6° C.) and then the reverse blend with the highest average elution temperature (98.3° C.). The profiles observed for the average elution temperatures of the different MW fractions correspond well with the expected trends of conventional, flat, and reverse distributions of comonomer. The comonomer level can also be represented as the amount of short chain branching. The TREF elution temperatures can also be calibrated (from the NMR results of a known standard) to the particular level of short chain branching present. The level of short chain branching (SCB) measured in short chain branches/1000C's for these 1-hexene copolymer blends is also determined. For these blends, the SCB level ranges from 1.4 to 3 SCB/1000C's which is equivalent to a range of 0.8 to 1.8 weight percent hexene. The values obtained using the instant invention differ little from the NMR measured values. Overall, reverse crossfractionation is highly sensitive to resins with very low amounts of comonomer. The technique is sensitive enough to detect subtle changes with less than 3 wt percent 1-hexene comonomer and can differentiate conventional, flat, and reverse placement of comonomer.

CONCLUSION

While the instant invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

The invention claimed is:

1. A method for GPC/TREF characterization of a polymer sample, comprising the steps of: (a) introducing a sample of a polymer to be characterized into a stream of eluent flowing through a gel permeation chromatography column to produce successive elution volumes from the gel permeation chromatography column wherein the polymer sample elutes therefrom substantially according to the molecular weight distribution of the polymer sample; (b) flowing a first elution volume from the gel permeation chromatography column into a first in-line TREF column at an elevated temperature; (c) flowing a second elution volume from the gel permeation chromatography column into a second in-line TREF column at an elevated temperature; (d) cooling the first TREF column to precipitate polymer in the first elution volume in the first TREF column; (e) cooling the second TREF column to precipitate polymer in the second elution volume in the second TREF column; (f) flowing a stream solvent through the second TREF column while heating the second TREF column to dissolve the polymer precipitated therein into the flowing stream of solvent; (g) flowing the stream of solvent from the second TREF column of step (f) through a flow through detector to detect the polymer in the stream of solvent as the polymer dissolves in the solvent as the second TREF column is heated; (h) flowing a stream solvent through the first TREF column while heating the first TREF column to dissolve the polymer precipitated therein into the flowing stream of solvent; (i) flowing the stream of solvent from the first TREF column of step (h) through a flow through detector of step (g) to detect the polymer in the stream of solvent as the polymer dissolves in the solvent as the first TREF column is heated.

2. The method of claim 1, wherein the flow through detector is selected from the group consisting of an infrared detector, a light scattering detector and a viscosity detector.

3. The method of claim 1, wherein the flow through detector is followed by two additional flow through detectors selected from the group consisting of an infrared detector, a light scattering detector and a viscosity detector.

4. Apparatus capable of being used for GPC/TREF characterization of a polymer sample or for TREF/GPC characterization of a polymer sample, the apparatus comprising: (a) an eluent reservoir; (b) a pump in liquid communication with the eluent reservoir; (c) a sample injection valve in liquid communication with the pump; (d) a two position six-port valve in liquid communication with the sample injection valve; (e) a gel permeation chromatography column having an inlet and an outlet, the inlet being in liquid communication with the six-port valve, the outlet being in liquid communication with the six-port valve; (f) a flow-through infrared detector in fluid communication with the six-port valve; (g) a flow-through light scattering detector in liquid communication with the infra-red detector; (h) a flow-through viscosity detector in liquid communication with the light scattering detector; (i) a waste reservoir in liquid communication with the viscosity detector; (j) a first tee in liquid communication with the six-port valve; (k) a first on-off valve in liquid communication with the first tee; (l) a second tee in liquid communication with the six-port valve and with the first on-off valve; (m) a first oven containing elements (c)-(h) and (j) and (l); (n) a two position three port valve in liquid communication with the first tee; (o) a cross in liquid communication with the three-port valve; (p) a first temperature equilibrium conduit in liquid communication at one end thereof with the three port valve; (q) a second temperature equilibrium conduit in liquid communication at one end thereof with the cross and at the other end thereof with the other end of the first temperature equilibrium conduit; (r) a third tee in liquid communication with the first cross; (s) a fourth tee in liquid communication with the third tee; (t) a second on-off valve in liquid communication with the fourth tee; (u) a second oven containing elements (n), (o), and (q)-(t); (v) a third on-off valve in liquid communication with the first cross; (w) a fourth on-off valve in liquid communication with the third tee; (x) a fifth on off valve in liquid communication with the fourth tee; (y) a first TREF column having an inlet and an outlet, the inlet of the first TREF column being in liquid communication with the third on-off valve; (z) a second TREF column having an inlet and an outlet, the inlet of the second TREF column being in liquid communication with the fourth on-off valve; (a') a third TREF column having an inlet and an outlet, the inlet of the third TREF column being in liquid communication with the fifth on-off valve; (b') a fifth tee in liquid communication with the outlet of the first TREF column and with the second tee; (c') a sixth tee in liquid communication with the outlet of the second TREF column and with the fifth tee; (d') a seventh tee in liquid communication with the outlet of the third TREF column and the second on-off valve as well as the sixth tee; (e') a third oven containing elements (v) and (y); (f') a fourth oven for containing elements (w) and (z'); (g') a fifth oven for containing elements (x) and (a'); (h') a sixth oven for containing elements (b'), (c') and (d'); and (I') a seventh oven for containing a portion of the liquid connection between (t) and (d').

\* \* \* \* \*